United States Patent [19]

Cowling

[11] Patent Number: 4,845,196

[45] Date of Patent: Jul. 4, 1989

[54] MODIFIED INTERFERON GAMMAS

[75] Inventor: Graham J. Cowling, Oxford, England

[73] Assignee: G. D. Searle & Co., Chicago, Ill.

[21] Appl. No.: 747,596

[22] Filed: Jun. 24, 1985

[51] Int. Cl.$^4$ .................. C07K 13/00; C07K 15/26; A61K 45/02; C12P 21/00

[52] U.S. Cl. .................. 530/351; 424/85.5; 435/68; 435/811

[58] Field of Search .................. 424/85, 85.5; 435/68, 435/172.3; 530/351

[56] References Cited

U.S. PATENT DOCUMENTS 4,457,867  7/1984  Ishida .................. 530/351
4,727,138  2/1988  Goeddel et al. .................. 435/68

FOREIGN PATENT DOCUMENTS 089626   9/1983  European Pat. Off. .
83/04053 11/1983  PCT Int'l Appl. .

OTHER PUBLICATIONS

Brewer et al, Trends in Biotechnology, vol. 3, pp. 119–122, 1985.
Devos et al., Nucleic Acid Research, vol. 10, pp. 2487–2501, 1982.
Gray et al., Nature, vol. 295, pp. 503–500, 1982.

Primary Examiner—Blondel Hazel
Attorney, Agent, or Firm—Mary Jo Kanady; Paul D. Matukaitis

[57] ABSTRACT

Described are modified human gamma interferons, genes coding for their synthesis and plasmids containing and capable of expressing these genes.

3 Claims, 1 Drawing Sheet

MODIFIED INTERFERON GAMMAS

BACKGROUND OF THE INVENTION

1. Field of The Invention

Described are novel polypeptides, DNA sequences and plasmids relating to novel modified human gamma-like interferons useful in pharmaceutical compositions.

2. Background of The Invention

Interferons (IFNs) are a family of proteins synthesised in mammalian cells in response to stimulation by viruses, mitogens and a variety of other substances. Initial studies on interferon concentrated on its ability to induce an antiviral state in target cells. More recently, interferon has been shown to inhibit cell proliferation and to modulate the immune response (1).

The interferons have potential used in the treatment of viral infections and malignant disease. The natural amino acid sequence and DNA sequence of Human Immune (gamma) Interferon was diclosed in UK patent application No. GB 2 107 718 A and European patent application No. 0088540A2.

Human interferons have been classified into 3 groups according to their antigenic, biological and chemical properties: IFN-alpha (leucocyte), IFN-beta (fibroblast) and IFN-gamma (immune). The virus induced, acid stable interferons (IFN-alpha and IFN-beta) have been studied in the greatest detail. The use of recombinant DNA technology has allowed the deduction of amino acid sequences of IFN-beta and several species of IFN-alpha. IFN-gamma is acid labile and does not cross react with antisera to IFN-alpha and IFN-beta. IFN-gamma possesses a wide range of biological activities (2,3,4). IFN-gamma potentiates the antiviral activity of IFN-alpha and IFN-beta but differs from the acid stable interferons in its virus and target cell specificity (2). However, in vitro studies with impure IFN-gamma indicate that one important activity of IFN-gamma is to regulate the immune response (3). Since the anti-proliferative effect of IFN-gamma on transformed cells is up to 100X that of either IFN-alpha or IFN-beta (4), IFN-gamma may be useful in the treatment of malignant disease. Mouse IFN-gamma shows significant anti-tumour activity against mouse sarcoma (5). The cDNA coding for human IFN-gamma has been cloned in *E. coli* (6,7). The amino acid sequence of IFN-gamma has been deduced and it has been shown that the mature polypeptide is 146 amino acids long. IFN-gamma has been expressed in *E. coli* and in a eukaryotic system (6). The levels of expression are much lower than those observed with IFN-alpha and IFN-beta in similar expression systems.

Modified interferon gammas have been described that contain a deleted cys-1, tyr-2, cys-3 (PCT application No. 83/04053). However, they do not disclose the modified interferon gammas of the present invention.

The synthetic human gamma interferon gene in plasmid pCC 203 was previously disclosed and deposited in the American type culture collection as ATCC 39494.

The addition of polyarginine to polypeptides to facilitate purification was previously described (8).

SUMMARY OF THE INVENTION

One object of the invention is the production of the modified human interferons IFNX 930, IFNX 955, IFNX 956, IFNX 957, and IFNX 958. Another object of the invention is the construction of genes coding for these modified gamma interferons and of plasmids capable of expressing these genes, resulting in the synthesis of the modified interferons.

Yet another object of the invention is the addition of polyarginine to the modified gamma interferons to facilitate purification.

Still another object of the invention is pharmaceutical compositions incorporating a therapeutically effective amount of the modified gamma interferons suitable for administration as antiviral, antiproliferative or immunoregulatory activity.

BRIEF DESCRIPTION OF THE CHARTS AND FIGURE DRAWINGS

Chart 1: The IFNX 930 gene showing the nucleotide sequence and the protein sequence. Mutagenesis involving C to T changes at Gly-34 to Asp-34 and Asp-66 to Asn-66 are shown.

Chart 2: The IFNX 955 gene showing the nucleotide and protein sequences. IFNX 955 is derived from IFNX 930 gene by the removal of Cys-1, Tyr-2 and Cys-3 amino acids.

Chart 3: The IFNX 930 gene with a six polyarginine tail showing nucleotide and protein sequence.

Chart 4: The IFNX 956 gene showing the nucleotide and protein sequence IFNX 956 is derived from IFN-gamma by a C to T change at Gly-34 to Asp-34.

Chart 5: The IFNX 957 gene showing the nucleotide and protein sequence. IFNX 957 is derived from IFN-gamma by a C to T change to Asp-66 to Asn-66.

Chart 6: The IFN-gamma gene with a six polyarginine tail showing the nucleotide and protein sequence.

Chart 7: The IFNX 918 showing the nucleotide and protein sequence.

FIG. 1: This shows the overall strategy for producing C to T changes in the human IFN-gamma gene by sodium bisuolphite mutagenesis.

DESCRIPTION OF THE PREFERRED EMBODIMENTS

Figure 1:
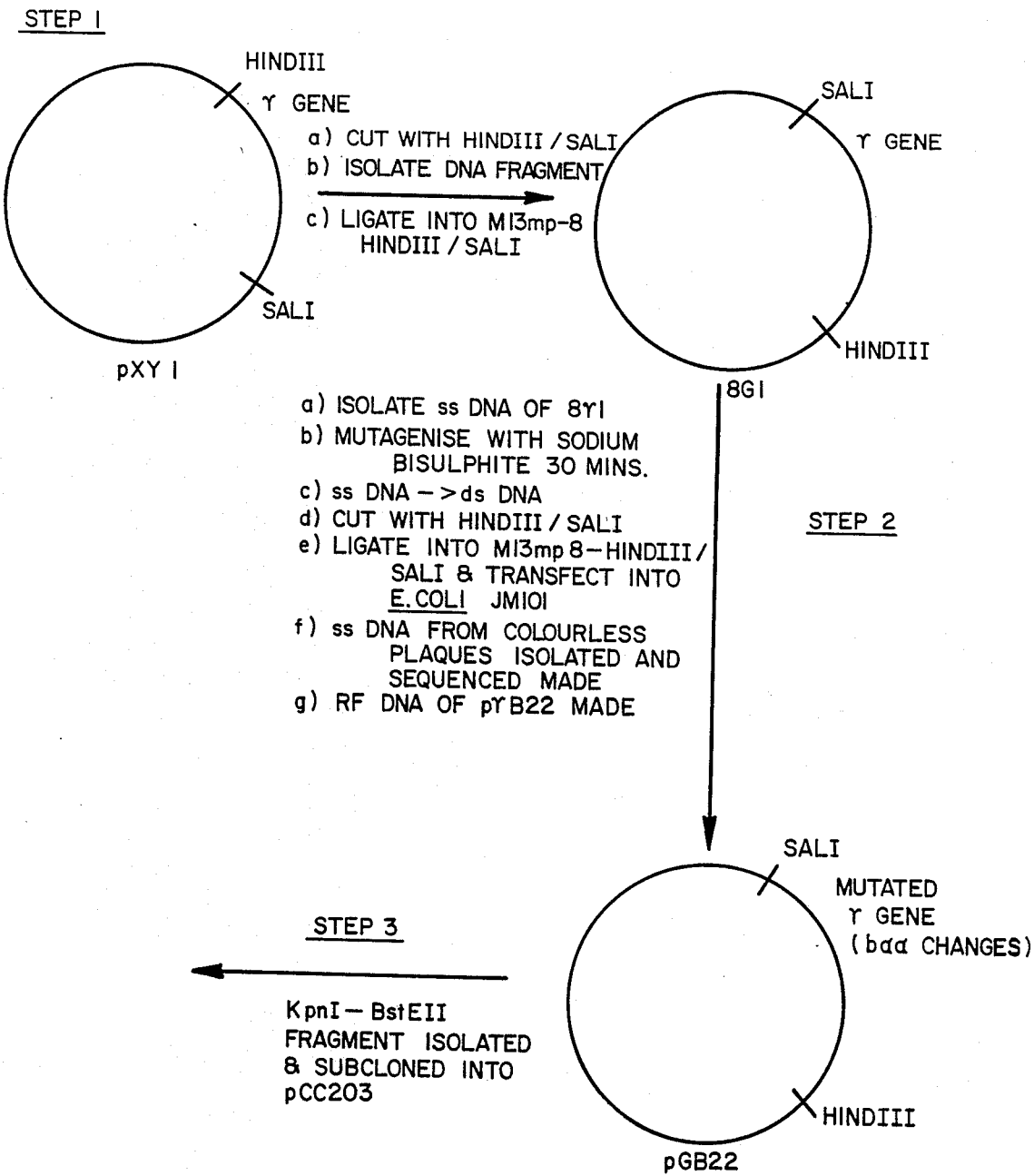

The modified human gamma interferons were produced by the bisulfate mutagenesis of the synthetic gamma gene isolated from pCC203. The resulting modified gamma interferon, IFNX 930, (Chart 1) was further modified to revmove cys-1, tyr-2, cys-3 to give IFNX 955 (Chart 2). IFNX 930 was modified to add the 6 arginine tail to facilitate purification resulting in the structure in Chart 3. IFNX 930 with a gly-34 to asp-34 change gave IFNX 956 (Chart 4). IFNX 930 with a asp-66 to asn-66 change gave IFNX 957 (Chart 5). Chart 6 shows the complete gamma interferon with a six arginine tail. Chart 7 shows a complete gamma interferon minus the cys-1, tyr-2, cys-3.

CHART 1

Amino Acid Sequence of IFNX 930 and DNA Sequence coding for its synthesis.

IFNγ[Gly34→Asp][Asp66→Asn]
MET—CYS—TYR—CYS—GLN—ASP—PRO—TYR—VAL—LYS—GLU—ALA—
GLU—ASN—LEU—
ATG TGT TAT TGT CAG GAT CCA TAC GTT AAA GAA GCT GAA AAC CTG
LYS—LYS—TYR—PHE—ASN—ALA—GLY—HIS—SER—ASP—VAL—ALA—

CHART 1-continued

Amino Acid Sequence of IFNX 930 and DNA Sequence coding for its synthesis.

ASP—ASN—GLY—
AAA AAA TAC TTC AAC GCA GGT CAC TCT GAC GTA GCA GAC AAC GGT
THR—LEU—PHE—LEU—ASP—ILE—LEU—LYS—ASN—TRP—LYS—GLU—
GLU—SER—ASP—
ACC CTG TTC CTC GAT ATC CTG AAA AAC TGG AAA GAA GAA AGC GAT
ARG—LYS—ILE—MET—GLN—SER—GLN—ILE—VAL—SER—PHE—TYR—
PHE—LYS—LEU—
CGT AAA ATC ATG CAG TCT CAG ATC GTA TCT TTC TAC TTC AAG CTG
PHE—LYS—ASN—PHE—LYS—ASP—ASN—GLN—SER—ILE—GLN—
LYS—SER—VAL—GLU—
TTC AAA AAC TTC AAA GAT AAT CAG TCG ATC CAA AAA TCC GTT GAA
THR—ILE—LYS—GLU—ASP—MET—ASN—VAL—LYS—PHE—PHE—ASN—
SER—ASN—LYS—
ACT ATC AAA GAA GAC ATG AAC GTA AAA TTC TTC AAC TCT AAC AAA
LYS—LYS—ARG—ASP—ASP—PHE—GLU—LYS—LEU—THR—ASN—
TYR—SER—VAL—THR—
AAG AAG CGC GAT GAC TTT GAA AAA CTG ACT AAC TAC TCG GTG ACC
ASP—LEU—ASN—VAL—GLN—ARG—LYS—ALA—ILE—HIS—
GLU—LEU—ILE—GLN—VAL—
GAC CTG AAC GTA CAG CGT AAA GCT ATC CAC GAG CTC ATT CAG GTT
MET—ALA—GLU—LEU—SER—PRO—ALA—ALA—LYS—THR—GLY—LYS—
ARG—LYS—ARG—
ATG GCA GAA CTG TCT CCA GCT GCA AAA ACT GGC AAA CGT AAA AGA
SER—GLN—MET—LEU—PHE—ARG—GLY—ARG—ARG—ALA—SER—GLN—***—
TCT CAG ATG CTG TTT CGT GGT CGC CGT GCT TCT CAG TAA
MCYCQDPYVK—EAENLKKYFN—AGHSDVADNG—TLFLDILKNW—
KEESDRKIMQ—
SQIVSFYFKL—FKNFKDNQSI—QKSVETIKED—MNVKFFNSNK—KKRDDFEKLT—
NYSVTDLNVQ—RKAIHELIQV—MAELSPAAKT—GKRKRSQMLF—RGRRASQ<

CHART 2

Amino Acid Sequence of IFNX 955 and DNA Sequence coding for its synthesis.

IFNγ[4-146][Gly34→Asp][Asp66→Asn]
MET—GLN—ASP—PRO—TYR—VAL—LYS—GLU—ALA—GLU—
ASN—LEU—LYS—LYS—TYR—
ATG CAG GAT CCA TAC GTT AAA GAA GCT GAA AAC CTG AAA AAA TAC
PHE—ASN—ALA—GLY—HIS—SER—ASP—VAL—ALA—ASP—ASN—GLY—
THR—LEU—PHE—
TTC AAC GCA GGT CAC TCT GAC GTA GCA GAC AAC GGT ACC CTG TTC
LEU—ASP—ILE—LEU—LYS—ASN—TRP—LYS—GLU—GLU—SER—ASP—
ARG—LYS—ILE—
CTC GAT ATC CTG AAA AAC TGG AAA GAA GAA AGC GAT CGT AAA ATC
MET—GLN—SER—GLN—ILE—VAL—SER—PHE—TYR—PHE—LYS—LEU—
PHE—LYS—ASN—
ATG CAG TCT CAG ATC GTA TCT TTC TAC TTC AAG CTG TTC AAA AAC
PHE—LYS—ASP—ASN—GLN—SER—ILE—GLN—LYS—SER—VAL—GLU—
THR—ILE—LYS—
TTC AAA GAT AAT CAG TCG ATC CAA AAA TCC GTT GAA ACT ATC AAA
GLU—ASP—MET—ASN—VAL—LYS—PHE—PHE—ASN—SER—
ASN—LYS—LYS—ARG—
GAA GAC ATG AAC GTA AAA TTC TTC AAC TCT AAC AAA AAG AAG CGC
ASP—ASP—PHE—GLU—LYS—LEU—THR—ASN—TYR—SER—VAL—THR—
ASP—LEU—ASN—
GAT GAC TTT GAA AAA CTG ACT AAC TAC TCG GTG ACC GAC CTG AAC
VAL—GLN—ARG—LYS—ALA—ILE—HIS—GLU—LEU—ILE—
GLN—VAL—MET—ALA—GLU—
GTA CAG CGT AAA GCT ATC CAC GAG CTC ATT CAG GTT ATG GCA GAA
LEU—SER—PRO—ALA—ALA—LYS—THR—GLY—LYS—ARG—LYS—ARG—
SER—GLN—MET—
CTG TCT CCA GCT GCA AAA ACT GGC AAA CGT AAA AGA TCT CAG ATG
LEU—PHE—ARG—GLY—ARG—ARG—ALA—SER—GLN—***—
CTG TTT CGT GGT CGC CGT GCT TCT CAG TAA
MQDPYVKEAE—NLKKYFNAGH—SDVADNGTLF—LDILKNWKEE—
SDRKIMQSQI—
VSFYFKLFKN—FKDNQSIQKS—VETIKEDMNV—KFFNSNKRR—
DDFEKLTNYS—
VTDLNVQRKA—IHELIQVMAE—LSPAAKTGKR—KRSQMLFRGR—RASQ<

CHART 3

Amino Acid Sequence of IFNX 930 plus six arginines and DNA Sequence coding for its synthesis.

MET—CYS—TYR—CYS—GLN—ASP—PRO—TYR—VAL—LYS—GLU—ALA—
GLU—ASN—LEU—
ATG TGT TAT TGT CAG GAT CCA TAC GTT AAA GAA GCT GAA AAC CTG
LYS—LYS—TYR—PHE—ASN—ALA—GLY—HIS—SER—ASP—VAL—ALA—
ASP—ASN—GLY—
AAA AAA TAC TTC AAC GCA GGT CAC TCT GAC CTA GCA GAC AAC GGT

CHART 3-continued

Amino Acid Sequence of IFNX 930 plus six arginines and DNA Sequence coding for its synthesis.

```
THR—LEU—PHE—LEU—ASP—ILE—LEU—LYS—ASN—TRP—LYS—GLU—
GLU—SER—ASP—
ACC CTG TTC CTC GAT ATC CTG AAA AAC TGG AAA GAA GAA AGC GAT
ARG—LYS—ILE—MET—GLN—SER—GLN—ILE—VAL—SER—PHE—TYR—
PHE—LYS—LEU—
CGT AAA ATC ATG CAG TCT CAG ATC GTA TCT TTC TAC TTC AAG CTG
PHE—LYS—ASN—PHE—LYS—ASP—ASN—GLN—SER—ILE—
GLN—LYS—SER—VAL—GLU—
TTC AAA AAC TTC AAA GAT AAT CAG TCG ATC CAA AAA TCC GTT GAA
THR—ILE—LYS—GLU—ASP—MET—ASN—VAL—LYS—PHE—PHE—
ASN—SER—ASN—LYS—
ACT ATC AAA GAA GAC ATG AAC GTA AAA TTC TTC AAC TCT AAC AAA
LYS—LYS—ARG—ASP—ASP—PHE—GLU—LYS—LEU—THR—
ASN—TYR—SER—VAL—THR—
AAG AAG CGC GAT GAC TTT GAA AAA CTG ACT AAC TAC TCG GTG ACC
ASP—LEU—ASN—VAL—GLN—ARG—LYS—ALA—ILE—HIS—
GLU—LEU—ILE—GLN—VAL—
GAC CTG AAC GTA CAG CGT AAA GCT ATC CAC GAG CTC ATT CAG GTT
MET—ALA—GLU—LEU—SER—PRO—ALA—ALA—LYS—THR—GLY—LYS—
ARG—LYS—ARG—
ATG GCA GAA CTG TCT CCA GCT GCA AAA ACT GGC AAA CGT AAA AGA
SER—GLN—MET—LEU—PHE—ARG—GLY—ARG—ARG—ALA—SER—GLN—ARG—ARG—
TCT CAG ATG CTG TTT CGT GGT CGC CGT GCT TCT CAG CGT CGA CGC
ARG—ARG—***—
CGT CGA CGT TAA
MCYCQDPYVK—EAENLKKYFN—AGHSDVADNG—TLFLDILKNW—
KEESDRKIMQ—
SQIVSFYFKL—FKNFKDNQSI—QKSVETIKED—MNVKFFNSNK—KKRDDFEDLT—
NYSVTDLNVQ—RKAIHELIQV—MAELSPAAKT—GKRKRSQMLF—
RGRRASQRRR—
```

CHART 4

Amino Acid Sequence of IFNX 956 and DNA Sequence coding for its synthesis.

```
IFNγ[Gly34→Asp]
MET—CYS—TYR—CYS—GLN—ASP—PRO—TYR—VAL—LYS—GLU—ALA—
GLU—ASN—LEU—
ATG TGT TAT TGT CAG GAT CCA TAC GTT AAA GAA GCT GAA AAC CTG
LYS—LYS—TYR—PHE—ASN—ALA—GLY—HIS—SER—ASP—VAL—ALA—
ASP—ASN—GLY—
AAA AAA TAC TTC AAC GCA GGT CAC TCT GAC GTA GCA GAC AAC GGT
THR—LEU—PHE—LEU—ASP—ILE—LEU—LYS—ASN—TRP—LYS—GLU—
GLU—SER—ASP—
ACC CTG TTC CTC GAT ATC CTG AAA AAC TGG AAA GAA GAA AGC GAT
ARG—LYS—ILE—MET—GLN—SER—GLN—ILE—VAL—SER—PHE—TYR—
PHE—LYS—LEU—
CGT AAA ATC ATG CAG TCT CAG ATC GTA TCT TTC TAC TTC AAG CTG
PHE—LYS—ASN—PHE—LYS—ASP—ASP—GLN—SER—ILE—
GLN—LYS—SER—VAL—GLU—
TTC AAA AAC TTC AAA GAT GAT CAG TCG ATC CAA AAA TCC GTT GAA
THR—ILE—LYS—GLU—ASP—MET—ASN—VAL—LYS—PHE—PHE—ASN—
SER—ASN—LYS—
ACT ATC AAA GAA GAC ATG AAC GTA AAA TTC TTC AAD TCT AAC AAA
LYS—LYS—ARG—ASP—ASP—PHE—GLU—LYS—LEU—THR—ASN—
TYR—SER—VAL—THR—
AAG AAG CGC GAT GAC TTT GAA AAA CTG ACT AAC TAC TCG GTG ACC
ASP—LEU—ASN—VAL—GLN—ARG—LYS—ALA—ILE—HIS—
GLU—LEU—ILE—GLN—VAL—
GAC CTG AAC GTA CAG CGT AAA GCT ATC CAC GAG CTC ATT CAG GTT
MET—ALA—GLU—LEU—SER—PRO—ALA—ALA—LYS—THR—GLY—LYS—
ARG—LYS—ARG—
ATG GCA GAA CTG TCT CCA GCT GCA AAA ACT GGC AAA CGT AAA AGA
SER—GLN—MET—LEU—PHE—ARG—GLY—ARG—ARG—ALA—SER—GLN—***—
TCT CAG ATG CTG TTT CGT GGT CGC CGT GCT TCT CAG TAA
MCYCQDPYVK—EAENLKKYFN—AGHSDVADNG—TLFLDILKNW—
KEESDRKIMQ—
SQIVSFYFKL—FKNFKDDQSI—QKSVETIKED—MNVKFFNSNK—KKRDDFEKLT—
NYSVTDLNVQ—RKAIHELIQV—MAELSPAAKT—GKRKRSQMLF—RGRRASQ<
```

CHART 5

Amino Acid Sequence of IFNX 957 and DNA Sequence coding for its synthesis.

```
IFNγ[Asp66→Asn]
MET—CYS—TYR—CYS—GLN—ASP—PRO—TYR—VAL—LYS—GLU—ALA—
GLU—ASN—LEU—
ATG TGT TAT TGT CAG GAT CCA TAC GTT AAA GAA GCT GAA AAC CTG
LYS—LYS—TYR—PHE—ASN—ALA—GLY—HIS—SER—ASP—VAL—ALA—
```

CHART 5-continued

Amino Acid Sequence of IFNX 957 and DNA Sequence coding for its synthesis.

ASP—ASN—GLY—
AAA AAA TAC TTC AAC GCA GGT CAC TCT GAC GTA GCA GAC AAC GGT
THR—LEU—PHE—LEU—GLY—ILE—LEU—LYS—ASN—TRP—LYS—GLU—
GLU—SER—ASP—
ACC CTG TTC CTC GGT ATC CTG AAA AAC TGG AAA GAA GAA AGC CAT
ARG—LYS—ILE—MET—GLN—SER—GLN—ILE—VAL—SER—PHE—TYR—
PHE—LYS—LEU—
CGT AAA ATC ATG CAG TCT CAG ATC GTA TCT TTC TAC TTC AAG CTG
PHE—LYS—ASN—PHE—LYS—ASP—ASN—GLN—SER—ILE—GLN—
LYS—SER—VAL—GLU—
TTC AAA AAC TTC AAA GAT AAT CAG TCG ATC CAA AAA TCC GTT GAA
THR—ILE—LYS—GLU—ASP—MET—ASN—VAL—LYS—PHE—PHE—ASN—
SER—ASN—LYS—
ACT ATC AAA GAA GAC ATG AAC GTA AAA TTC TTC AAC TCT AAC AAA
LYS—LYS—ARG—ASP—ASP—PHE—GLU—LYS—LEU—THR—ASN—
TYR—SER—VAL—THR—
AAG AAG CGC GAT GAC TTT GAA AAA CTG ACT AAC TAC TCG GTG ACC
ASP—LEU—ASN—VAL—GLN—ARG—LYS—ALA—ILE—HIS—
GLU—LEU—ILE—GLN—VAL—
GAC CTG AAC GTA CAG CGT AAA GCT ATC CAC GAG CTC ATT CAG GTT
MET—ALA—GLU—LEU—SER—PRO—ALA—ALA—LYS—THR—GLY—LYS—
ARG—LYS—ARG—
ATG GCA GAA CTG TCT CCA GCT GCA AAA ACT GGC AAA CGT AAA AGA
SER—GLN—MET—LEU—PHE—ARG—GLY—ARG—ARG—ALA—SER—GLN—***—
TCT CAG ATG CTG TTT CGT GGT CGC CGT GCT TCT CAG TAA
MCYCQDPYVK—EAENLKKYFN—AGHSDVADNG—TLFLGILKNW—
KEESDRKIMQ—
SQIVSFYFKL—FKNFKDNQSI—QKSVETIKED—MNVKFFNSNK—KKRDDFEKLT—
NYSVTDLNVQ—RKAIHELIQV—MAELSPAAKT—GKRKRSQMLF—RGRRASQ<

CHART 6

Amino Acid Sequence of Interferon Gamma plus six arginines and DNA Sequence coding for its synthesis.

IFNγ Synthetic + Arg(6)
MET—CYS—TYR—CYS—GLN—ASP—PRO—TYR—VAL—LYS—GLU—ALA—
GLU—ASN—LEU—
ATG TGT TAT TGT CAG GAT CCA TAC GTT AAA GAA GCT GAA AAC CTG
LYS—LYS—TYR—PHE—ASN—ALA—GLY—HIS—SER—ASP—VAL—ALA—
ASP—ASN—GLY—
AAA AAA TAC TTC AAC GCA GGT CAC TCT GAC GTA GCA GAC AAC GGT
THR—LEU—PHE—LEU—GLY—ILE—LEU—LYS—ASN—TRP—LYS—GLU—
GLU—SER—ASP—
ACC CTG TTC CTC GGT ATC CTG AAA AAC TGG AAA GAA GAA AGC GAT
ARG—LYS—ILE—MET—GLN—SER—GLN—ILE—VAL—SER—PHE—TYR—
PHE—LYS—LEU—
CGT AAA ATC ATG CAG TCT CAG ATC GTA TCT TTC TAC TTC AAG CTG
PHE—LYS—ASN—PHE—LYS—ASP—ASP—GLN—SER—ILE—GLN—
LYS—SER—VAL—GLU—
TTC AAA AAC TTC AAA GAT GAT CAG TCG ATC CAA AAA TCC GTT GAA
THR—ILE—LYS—GLU—ASP—MET—ASN—VAL—LYS—PHE—PHE—ASN—
SER—ASN—LYS—
ACT ATC AAA GAA GAC ATG AAC GTA AAA TTC TTC AAC TCT AAC AAA
LYS—LYS—ARG—ASP—ASP—PHE—GLU—LYS—LEU—THR—ASN—
TYR—SER—VAL—THR—
AAG AAG CGC GAT GAC TTT GAA AAA CTG ACT AAC TAC TCG GTG ACC
ASP—LEU—ASN—VAL—GLN—ARG—LYS—ALA—ILE—HIS—
GLU—LEU—ILE—GLN—VAL—
GAC CTG AAC GTA CAG CGT AAA GCT ATC CAC GAG CTC ATT CAG GTT
MET—ALA—GLU—LEU—SER—PRO—ALA—ALA—LYS—THR—GLY—LYS—
ARG—LYS—ARG—
ATG GCA GAA CTG TCT CCA GCT GCA AAA ACT GGC AAA CGT AAA AGA
SER—GLN—MET—LEU—PHE—ARG—GLY—ARG—ARG—ALA—SER—GLN—
ARG—ARG—ARG—
TCT CAG ATG CTG TTT CGT GGT CGC CGT GCT TCT CAG CGT CGA CGC
ARG—ARG—ARG—***—
CGT CGA CGT TAA
MCYCQDPYVK—EAENLKKYFN—AGHSDVADNG—TLFLGIKNW—
KEESDRKIMQ—
SQIVSFYFKL—FKNFKDDQSI—QKSVETIKED—MNVKFFNSNK—KKRDDFEKLT—
NYSVTDLNVQ—RKAIHELIQV—MAELSPAAKT—GKRKRSQMLF—
RGRRASQRRR—

CHART 7

Amino Acid Sequence of IFNX 918 and DNA Sequence coding for its synthesis.

IFNγ[4-146]
MET—GLN—ASP—PRO—TYR—VAL—LYS—GLU—ALA—GLU—ASN—

CHART 7-continued

Amino Acid Sequence of IFNX 918 and DNA Sequence coding for its synthesis.

```
LEU—LYS—LYS—TYR—
ATG CAG GAT CCA TAC GTT AAA GAA GCT GAA AAC CTG AAA AAA TAC
PHE—ASN—ALA—GLY—HIS—SER—ASP—VAL—ALA—ASP—ASN—GLY—
THR—LEU—PHE—
TTC AAC GCA GGT CAC TCT GAC GTA GCA GAC AAC GGT ACC CTG TTC
LEU—GLY—ILE—LEU—LYS—ASN—TRP—LYS—GLU—GLU—SER—ASP—
ARG—LYS—ILE—
CTC GGT ATC CTG AAA AAC TGG AAA GAA GAA AGC GAT CGT AAA ATC
MET—GLN—SER—GLN—ILE—VAL—SER—PHE—TYR—PHE—LYS—LEU—
PHE—LYS—ASN—
ATG CAG TCT CAG ATC GTA TCT TTC TAC TTC AAG CTG TTC AAA AAC
PHE—LYS—ASP—ASP—GLN—SER—ILE—GLN—LYS—SER—VAL—GLU—
THR—ILE—LYS—
TTC AAA GAT GAT CAG TCG ATC CAA AAA TCC GTT GAA ACT ATC AAA
GLU—ASP—MET—ASN—VAL—LYS—PHE—PHE—ASN—SER—AS-
N—LYS—LYS—LYS—ARG—
GAA GAC ATG AAC GTA AAA TTC TTC AAC TCT AAC AAA AAG AAG CGC
ASP—ASP—PHE—GLU—LYS—LEU—THR—ASN—TYR—SER—VAL—THR—ASP—
LEU—ASN—
GAT GAC TTT GAA AAA CTG ACT AAC TAC TCG GTG ACC GAC CTG AAC
VAL—GLN—ARG—LYS—ALA—ILE—HIS—GLU—LEU—ILE—GL-
N—VAL—MET—ALA—GLU—
GTA CAG CGT AAA GCT ATC CAC GAG CTC ATT CAG CTT ATG GCA GAA
LEU—SER—PRO—ALA—ALA—LYS—THR—GLY—LYS—ARG—LYS—ARG—
SER—GLN—MET—
CTG TCT CCA GCT CGA AAA ACT GGC AAA CGT AAA AGA TCT CAG ATG
LEU—PHE—ARG—GLY—ARG—ARG—ALA—SER—GLN—***—
CTG TTT CGT GGT CGC CGT GCT TCT CAG TAA
MQDPYVKEAE—NLKKYFNAGH—SDVADNGTLF—LGILKNWEE—
SDRKIMQSQI—
VSFYFKLFKN—FKDDQSIQKS—VETIKEDMNV—KFFNSNKKR—
DDFEKLTNYS—
VTDLNVQRKA—IHELIQVMAE—LSPAAKTGKR—KRSQMLFRGR—RASQ<
```

The plasmids of Example 2 containing the genes of Example 1 code for the expression of the modified gamma interferons with the antiviral and antiproliferative activity described in Example 3. The DNA sequence described in the charts are only one sequence which is capable of coding for the given amino acid sequence. Given the multiple triplet codons for asp and asn, alternative DNA sequences can be constructed that code for the polypeptide sequence defined in the charts. It is possible to construct these alternative DNA sequences which would also code for the synthesis of the same amino acid sequence by inserting for asp-34 either GAT or GAA, and for asn-66, inserting either AAT or AAC.

EXAMPLE 1

Mutagenesis Procedure

Sodium bisulphite mutagenesis of a synthetic gamma gene to create a new gene which produced a novel gamma-IFN (IFN 930) (FIG. 1)

The nonsense strand of the synthetic gamma gene from pCC203 was mutagenised with sodium bisulphite in an M13 mp8 vector. Part of the mutated gene was susequently reconed into an IFN-gamma expression vector (pCC203) substituting the normal sequence for the mutated sequence. The procedure was as follows, and is illustrated in FIG. 1.

Step 1

The synthetic gamma gene (446 bp) from pCC203 (ATCC No. 39,494) was cut out using the restriction enzymes HindIII and SalI. The DNA was extracted from agarose gels (Molecular cloning, A Laboratory Manual, eds. Maniatis et al, p166, Cold Spring Harbor Laboratories 1982) and ligated into phage M13 mp8 vector (Sanger, F. et al, J. Mol. Biol., 143, 161, 1981) cut with HindIII and SalI (7213 bp), to give plasmid 8G1 (7659 bp).

Step 2

Single strand DNA of 8G1 was prepared using the protocol described by Amersham International, ss DNA of 8G1 contained the nonsense strand of the synthetic gamma gene. The ss DNA was mutagenised with sodium bisulphite for 30 minutes (Shortle and Botstein, Methods in Enzymology, 100, 457, 1983). The second strand DNA was made (published procedure of Amersham International) and the double stranded DNA was restricted with HindIII and SalI and ligated into the original M13 mp8 vector cut with HindIII and SalI. Ligated DNA was used to transfect $E.\ coli$ JM101 and ss DNA was prepared from colourless plaques and sequenced using the Sanger dideoxy method (Amersham procedure). A mutgenised clone encoding the following 6 amino acid mutations was identified; $Val_{25} \to Ile$, $Gly_{32} \to As$, $Asp_{66} \to Asn$, $Arg_{110} \to His$, $Ala_{127} \to Thr$, $Gly_{130} \to Ser$. A replicative form DNA of pGB22 was prepared.

Step 3

The DNA sequence encoding the $Gly_{34} \to Asp$, and $Asp_{66} \to Asn$ changes was isolated away from the other mutations in pGB22 on a KpnI-Bst EII fragment and subcloned into pCC203. The resulting plasmid was designated pXY12, and consists of the IFN-gamma gene (with the Asp-34 and Asn-66 mutations) under the control of the $E.\ coli$ trp promoter. The expressed protein was designated IFNX 930.

TABLE 1

Table of Plasmids

| Plasmid | Properties | Description |
|---------|-----------|-------------|
| pCC203  | Expression vector containing IFN-gamma gene | ATCC No. 39,494 |
| pXY12   | Expression vector containing | Chart 1 |

TABLE 1-continued

Table of Plasmids

| Plasmid | Properties | Description |
|---|---|---|
| | IFNX 930 gene | |
| pRC1 | Expression vector containing IFNX 955 gene | Chart 2 |
| pRC2 | Expression vector containing IFNX 930 + C-terminus 6 polyarginine tail | Chart 3 |
| pRC3 | Expression vector containing IFNX 930 gene with modified RBS-ATG sequence | Chart 1 |
| pRC4 | Expression vector containing IFNX 956 gene | Chart 4 |
| pRC5 | Expression vector containing IFNX 957 gene | Chart 5 |
| pCC20 | Expression vector containing IFN-gamma + C-terminus 6 polyarginine tail | Chart 6 |
| pJB9 | Expression vector containing IFNX 918 | Chart 7 |
| 8G1 | Bacteriophage M13 mp8 containing the synthetic IFN-gamma gene in pCC203 | FIG. 1 |
| pGB22 | Phage 8G1 having a mutagenised IFN-gamma gene | FIG. 1 |
| pAT153 | Subcloning plasmid | BRL Commercial |
| pCC703 | Expression vector containing IFN-gamma gene. Identical to pCC203 except for r.b.s.-ATG linker (Chart 2c) | |

EXAMPLE 2

Construction of Plasmids

Plasmids containing the IFNX 918 (pJB9) and IFNX 955 (pRC1) genes

The expression vector pCC 203 was digested with ClaI and BamH1 endonucleases and the resulting 4527 bp fragment was isolated by electrophoresis on agarose gel. Following calf intestial alkaline phosphatase treatment was ligated using T4 ligase with oligomers described in Table 2A, which had been phosphorylated using T4 kinase.

The ligation mixture was used to transform competent E. coli HB101 using standard transformation conditions. Following overnight culture on L-agar plates containing 100 ug/ml ampicillin, colonies corresponding to pJB9 were identified by restriction mapping and DNA sequencing.

The plasmid pRC1 was constructed by ligating the 4248 bp BstEII-BamH1 fragment of pJB9 with the 295 bp BamH1-BstEII fragment of pXY12 using T4 ligase. Part of this ligation mixture was used to transform competent E. coli HB101 using standard conditions. Colonies corresponding to pRC1 were identified by restriction mapping and DNA sequencing.

Plasmids containing the genes for IFN-gamma-polyarginine tail (pCC20) and IFNX930-polyarginine tail (pRC2)

The DNA duplex coding for IFN-gamma amino acids 136–146 followed by 6 arginine codons (Table 2b) was subconed into the EcoR1 and BamH1 sites of pAT153. The 247 bp BglII-SphI fragment corresponding to IFN-gamma amino acids 136–146, 6 arginine codons, a termination codon and the remaining sequence of the tetracycline resistance gene (BamH1 to SphI) was ligated into a 4319 bp SphI-BglII frgment of the pCC203. Clones of pCC20 were isolated following transformation into competent E. coli HB101 and characterised by restriction mapping and DNA sequencing.

The plasmid pRC2 was constructed by ligating the 1215 bp PstI-SacI fragment of pXY12 with the 3337 bp SacI-PstI fragment of pCC20 using T4 ligase. Clones of pRC2 were identified following transformation into completent E. coli HB101, by restriction mapping and DNA sequencing.

Plasmids containing the genes for IFNX 956 and IFNX 957

Because pXY12 has three PvuI sites; Ampicillin resistance gene, ribosome binding site and IFNX 930 gene, a further expression vector for IFNX 930 was constructed using a r.b.s.-ATG linker which did not contain a PvuI site. This used an expression vector for the synthetic IFN-gamma gene (pCC703) which is identical to pCC203 except for the ribosome binding site (r.b.s.)-ARG linker sequence (Table 2C).

The construction of pCC703 was similar to that of pJB9 except the oligomers described in Table 2C were used. The plasmid containing the IFNX 956 gene was built by ligating the 896 bp PvuI fragment of RC3 with the 3658 bp PvuI fragment of pCC703 using T4 ligase. RC4 cones were identified by restriction mapping and DNA sequencing. The plasmid containing the IFNX 957 gene was constructed by ligating the 896 bp PvuI frgment of pCC703 with the 3658 by PvuI fragment of pRC3, pRC5 clones were identified by restriction mapping and DNA sequencing.

Table 1 illustrates the oligonucleotide duplexes used to construct pJB9, B pCC20, pCC203, and pCC703. This shows (i) the estimated amount of expression in terms of % total bacterial protein, (ii) the antiviral activity as International units/liter/Optical density unit at 670 nm, and (iii) the antiproliferative activity as units/-liter/Optical density unit at 670 nm. Measurements (i) to (iii) are made using a crude bacterial lysate of expression vectors pCC203, pXY12, PCC20, pRC1, pJB9, pRC2, pRC3, pRC4, and pRC5 in E. coli HB101.

TABLE 2

A. Cla I
BamHI
CGATCGAATGCAG
TAGCTTACGTCCTAG
Oligonucleotides used in the construction of pJB9

B. EcoRI
AATTCAAACGTAAAAGATCTCAGATGCTGTTTCGTGGTCGCCGTGCTTCTCAGCGT
GTTTGCATTTTCTAGAGTCTACGACAAAGCACCAGCGGCACGAAGAGTCGCA
BamHI
CGACGCCGTCGACGTTAAG
GCTGCGGCAGCTGCAAATTCCTAG
DNA duplex used in the construction of pCC20

C. Ribosome binding site to ATG sequence used in constructions pCC203, pXY12, pRC1, pRC2, pRC3, pCC20 and pJB9.
CGATCGA.ATG.

TABLE 2-continued

Ribosome binding site to ATG sequence used in constructions pCC703, pRC3, pRC4 and pRC5.
CGATAAGCT.ATG

EXAMPLE 3

Expression of Interferon Genes and Biological Activity

Expression of modified IFN-gamma gene containing plasmids

Overnight cultures of plasmids were grown in M9 medium supplemented with tryptophan (40 ug/ml) and containing ampicillin (100 ug/ml). Innocula (0.5 ml) were added to m9 medium (50 ml, ampicillin 100 ug/ml). Growth was continued at 37° until the optical density at 670 nm had reached 0.5, at which time the cultures were made 20 ug/ml with respect to beta-indole acrylic acid (10 mg/ml in EtOH). Growth was continued at 37° with vigorous shaking and samples for assay and electrophoretic analysis were removed at 4 hours.

Assay of samples for interferon activity

Culture (10-20 ml) was removed as the optical density 670 nm of 1.5-2.0 (middle to late log phase of growth) and centrifuged to recover the cells. After suspension of 25 mM Tris-HCl ph7.5, 50 mM NaCl (1 ml) 1 mM EDTA at 0° (1.4 ml), 28 ul lysozyme was added to a final concentration of 50 ug/ml and the suspension incubated at 0° for 30 minutes. The suspension was sonicated for 24 seconds, the cell debris removed by centrifugation and the supernatants assayed for biological activity.

SDS Gel electrophoresis of samples for Interferon protein content

The volume of cells equivalent to 0.5 optical density units at 670 nm was removed from the culture and the cell recovered by centrifugation. The cells were immediately resuspended in 50 ul of 60 mM Tris-HCl pH6.8, 0.05% bromophenol blue, 5% glycerol, 1% sodium dodecyl sulphate, 0.5% bromophenol blue, 5% glycerol, 1% sodium dodecyl sulphate, 0.5% 2-mercaptoethanol, heated at 100° for 3 minutes and quick frozen on dry ice. The boiling-freezing cycles were repated 2-3 times to reduce the viscosity of the sample before a final boiling 5 minutes prior loading 7.5 ul on a 15% polyacrylamide gel prepared according to Laemmli. The protein estimate was made for the size of the band of IFN-gamma on these gels compared to total protein.

Biological Activity of Interferons

Antiviral Assay

The cellular extract was assayed for antiviral activity by monitoring the protectin conferred on Vero (African Green Monkey) cells against the cytopathic effect of EMC (Encephalomyocarditis) virus infection in an in vitro microplate assay system 9see, for example Dahl, H., and Degre, M., Path. Microbiol. Scan., 1380 (1972) 863).

Antiproliferative Assay

Antiproliferative activity of interferon was assessed in HEp-2 cells (human laryngeal carcinoma). Growth inhibition was measured by methylene blue staining of the cell monolayer by a modification of the method of Ito. (Ito, M. 1984, Microassay for studying anticullular effects of human interferons J. Interferon Res. 4 603-608) IC50 end point is the log dilution giving 50% reduction of methylene blue staining.

TABLE 3

| Plasmid | IFNX | Biological Activities and Expression Levels | | |
|---|---|---|---|---|
| | | Protein Estimate % Total Protein | AV Activity IU/OD/1 | AP Activity U/OD/1 |
| pCC203 | IFN-gamma | 5-10% | $1\text{-}13 \times 10^7$ | $5\text{-}10 \times 10^5$ |
| pXY12 | IFNX 930 | 5-10% | $33\text{-}62 \times 10^7$ | $20\text{-}50 \times 10^5$ |
| pCC20 | IFN-gamma ×6 arg | 5% | $5\text{-}6 \times 10^6$ | N.D. |
| pRC2 | IFNX 930 ×6 arg | 5% | $16\text{-}64 \times 10^6$ | $5 \times 10^5$ |
| pJB9 | IFNX 918 | 5-10% | $2\text{-}21 \times 10^7$ | $6 \times 10^5$ |
| pRC1 | IFNX 955 | 5-10% | $12\text{-}77 \times 10^7$ | $5 \times 10^5$ |
| pRC3 | IFNX 930 | 5-10% | $6\text{-}91 \times 10^7$ | N.D. |
| pRC4 | IFNX 956 | 5-10% | $8 \times 10^7$ | N.D. |
| pRC5 | IFNX 957 | 5-10% | $1 \times 10^7$ | N.D. |

N.D. Not determined
AV is antiviral
AP is antiproliferative

Results

Table 3 summarises the expression results using expression plasmids containing the modified IFN1-gamma genes. The international units of IFN are defined against and IFN-beta standard used as 3.23 units/ml. All cultures were 50 ml shaking flask, as described and 10 mls were removed for assay purposes. The antiviral activities shown in Table 3 are defined as International units of IFN antiviral activity per optical density at 670 nm of bacterial cells per liter of bacterial culture. The antiproliferative activities are expressed as units per optical density at 670 nm of bacterial cells per liter of bacterial culture.

Pharmaceutical compositions

The compounds of the present invention can be formulated according to known methods to prepare pharmaceutically useful compositions, whereby the human interferon gamma product is combined in admixture with a pharmaceutically acceptable carrier vehicle. Suitable vehicles and their formulation are described in Remington's *Pharmaceutical Sciences* by E. JW. Martin, which is hereby incorporated by reference. Such compositions will contain an effective amount of the interferon proteins of this invention in combination with a suitable amount of vehicle in order to prepare pharmaceutically acceptable compositions suitable for effective administration to the host.

Parenteral administration

The human interferon gamma composition may be parenterally administered to subjects requiring antitumour or antiviral treatment, and to those exhibiting immunosuppressive conditions. Dosage and dose rate may parallel that currently in use in clinical investigations of other human interferons, e.g., about $(1-10) \times 10^6$ units daily, and in the case of materials of purity greater than 1 percent, likely up to e.g., $50 \times 10^6$ units daily. As one example of an appropriate dosage form for essentially homogeneous IFN-gamma in parenteral form applicable, 3 mg. IFN-gamma of specific activity of, say, $2 \times 10^8$ U/mg may be dissolved in 25 ml. 5N serum albumin (human)-USP, the solution passed through a bacteriological filter and the filtered solution aseptically subdivided into 100 vials, each containing $6 \times 10^6$ units per interferon suitable for parenteral administration. The vials are preferably stored in the cold ($-20°$ C.) prior to use.

REFERENCES

1. Stewart, W. E. (1979) The Interferon System (Springer, New York).
2. Fleishmann, W. R., Georgiades, J. A., Osborne, L. L. and Johnson, H. M. (1979) Infect. Immun. 26, 248-253.
3. Rubin, B. Y. and Gupta, S. L. (1980) Proc. Nat. Acad. Sci. U.S.A. 77, 5928-5932.
4. Blulock, J. E., Georgiades, J. A., Langford, M. P. and Johnson, H. M. (1980) Cell. Immun. 49, 390-394.
5. Crane, J. L., Glasgow, L. A., Kern, E. R. and Youngner, J. S. (1978) J. natn. Cancer Inst. 61 871-874.
6. Gray, P. W., Leung, D. W., Pennica, D., Yelverton, E., Najarian, R., Simonsen, C. C., Derynck, R., Sherwood, P. J., Wallace, D. M., Berger, S. L., Levinson, A. D. and Goeddel, D. V. (1982) Nature 295, 503-508.
7. Devos, R., Cheroutre, H., Taya, Y., Degrave, W., Van Heuverswyn, H. and Fiers, W. (1982) Nucleic Acids Res. 8, 2487-2501.
8. Brewer, S. J. and Sassenfield, H. M., Trends in Biotechnology, Vol. 3, No. 5, 1985.

I claim:
1. A modified gamma interferon comprising IFNγ[Gly34→Asp][Asp 66→Asn].
2. A modified gamma interferon comprising IFNγ[4-146][Gly34→Asp][Asp66→Asn].
3. A modified gamma interferon comprising the modified gamma interferon of claim 1 having a polyarginine segment of from two to twelve arginine resid

UNITED STATES PATENT AND TRADEMARK OFFICE
CERTIFICATE OF CORRECTION

PATENT NO. : 4,845,196

DATED : July 4, 1989

INVENTOR(S) : Graham J. Cowling

It is certified that error appears in the above-identified patent and that said Letters Patent is hereby corrected as shown below:

Column 1, line 17, reading "used" should read -- uses --.
Column 2, line 41, reading "IFNX 918 showing" should read -- IFNX 918 gene showing --.
Column 2, line 53, reading "revmove" should read -- remove --.
Column 3, line 57, the amino acid sequence reading "-KFFNSNKRR-" should read -- -KFFNSNKKKR- --.
Column 7, line 59, the amino acid sequence reading "-TLFLGIKNW-" should read -- -TLFLGILKNW- --.
Column 9, line 22, the codon coding for amino acid VAL, reading "CTT" should read -- GTT --.
Column 9, line 27, reading "-LGILKNWEE-" should read -- -LGILKNWKEE- --.
Column 9, line 29, reading "-KFFNSNKKR-" should read -- -KFFNSNKKKR- --.
Column 9, line 57, reading "reconed" should read -- recloned --.
Column 10, line 50, reading "$Gly_{32}$" should read -- $Gly_{34}$ --.
Column 12, line 7, reading "subconed" should read -- subcloned --.
Column 12, line 12, reading "frgment" should read -- fragment --.
Column 12, line 38, reading "cones" should read -- clones --.
Column 12, line 41, reading "frgment" should read -- fragment --.
Column 12, line 41, reading "3658 by" should read -- 3658bp --.
Column 12, line 65, reading "GCTGCGGCAGCTGCAAATTCCTAG" should read -- GCTGCGGCAGCTGCAATTCCTAG --.
Column 13, line 15, reading "m9" should read -- M9 --.
Column 14, line 16, reading "9see" should read -- (see --.

UNITED STATES PATENT AND TRADEMARK OFFICE
CERTIFICATE OF CORRECTION

PATENT NO. : 4,845,196

DATED : July 4, 1989

INVENTOR(S) : Graham J. Cowling

It is certified that error appears in the above-identified patent and that said Letters Patent is hereby corrected as shown below:

Column 14, line 36, reading "X6 arg" should read -- +6 arg --.
Column 14, line 38, reading "X6 arg" should read -- +6 arg --.

Signed and Sealed this

Twenty-ninth Day of September, 1992

Attest:

DOUGLAS B. COMER

*Attesting Officer*          *Acting Commissioner of Patents and Trademarks*